(12) United States Patent
Boltanski et al.

(10) Patent No.: US 8,382,474 B2
(45) Date of Patent: Feb. 26, 2013

(54) DENTAL ARTICULATOR

(75) Inventors: Rami Boltanski, Kiryat Ono (IL); Nir Makmel, Tel Aviv (IL); Avi Kopelman, Tenafly, NJ (US)

(73) Assignee: Cadent Ltd., Or Yehuda (IL)

( * ) Notice: Subject to any disclaimer, the term of this patent is extended or adjusted under 35 U.S.C. 154(b) by 0 days.

(21) Appl. No.: 12/654,735

(22) Filed: Dec. 30, 2009

(65) Prior Publication Data

US 2010/0173258 A1    Jul. 8, 2010

Related U.S. Application Data

(60) Provisional application No. 61/193,867, filed on Dec. 31, 2008.

(51) Int. Cl.
*A61C 11/02* (2006.01)
(52) U.S. Cl. ............................................. 433/57; 432/61
(58) Field of Classification Search .................. 433/57, 433/49, 50, 53–56, 58–69
See application file for complete search history.

(56) References Cited

U.S. PATENT DOCUMENTS

| | | | | |
|---|---|---|---|---|
| 2,659,146 | A * | 11/1953 | Erickson et al. | 433/153 |
| 4,337,039 | A * | 6/1982 | Martin et al. | 433/60 |
| 4,728,330 | A * | 3/1988 | Comparetto | 623/18.11 |
| 5,385,470 | A | 1/1995 | Polz | |
| 5,586,884 | A * | 12/1996 | Kraus | 433/60 |
| 6,234,794 | B1 * | 5/2001 | Ozaki | 433/57 |
| 6,318,998 | B1 * | 11/2001 | Miller | 433/64 |
| 7,220,124 | B2 | 5/2007 | Taub et al. | |
| 7,686,278 | B2 * | 3/2010 | Lin | 249/54 |
| 7,857,622 | B2 * | 12/2010 | Lee | 433/57 |
| 2001/0029010 | A1 * | 10/2001 | Wells et al. | 433/49 |
| 2005/0282105 | A1 | 12/2005 | Callne | |
| 2006/0115784 | A1 * | 6/2006 | McMurtry et al. | 433/49 |
| 2006/0188838 | A1 | 8/2006 | Callne | |
| 2006/0204921 | A1 | 9/2006 | Uhm | |
| 2006/0210944 | A1 * | 9/2006 | Jung et al. | 433/57 |

* cited by examiner

*Primary Examiner* — Ralph Lewis
(74) *Attorney, Agent, or Firm* — Wilson Sonsini Goodrich & Rosati

(57) ABSTRACT

A dental articulator is provided in which at least one of the two arms thereof has a base member that is articulated with respect to a bracket element onto which a dental model may be mounted, allowing independent movement of the dental model with respect to the pivot axis hingedly linking the arms.

28 Claims, 11 Drawing Sheets

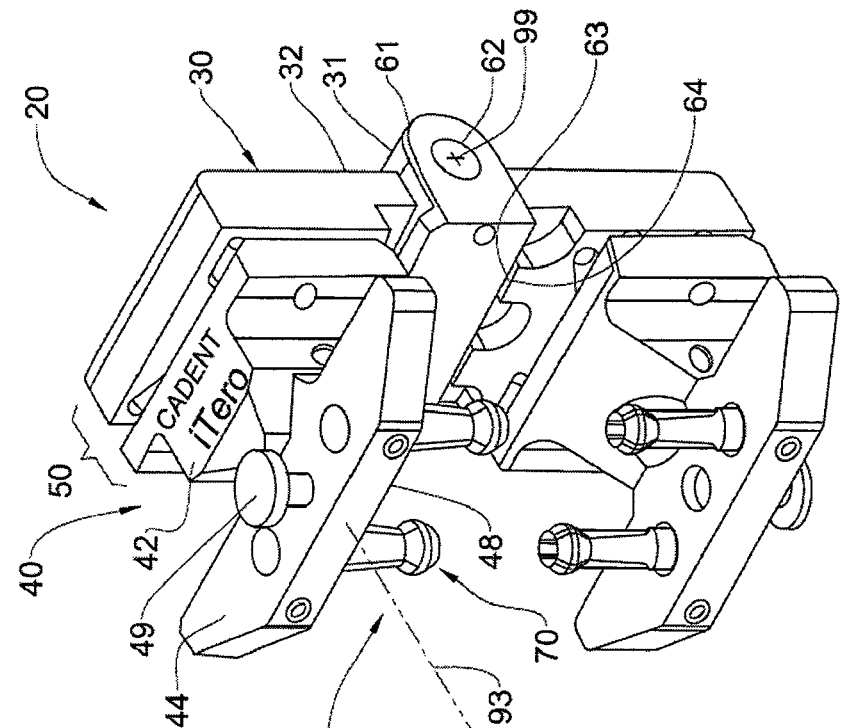
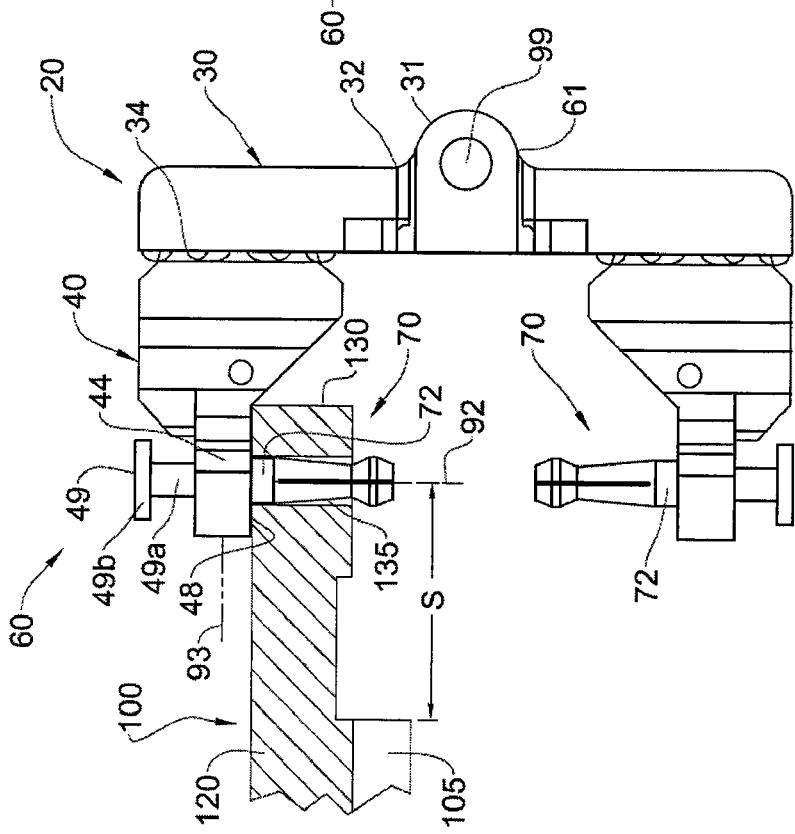
FIG. 3
FIG. 4

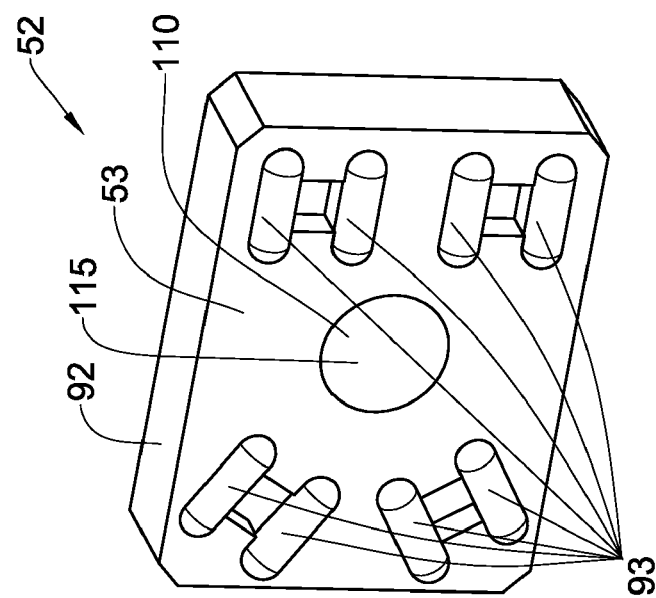
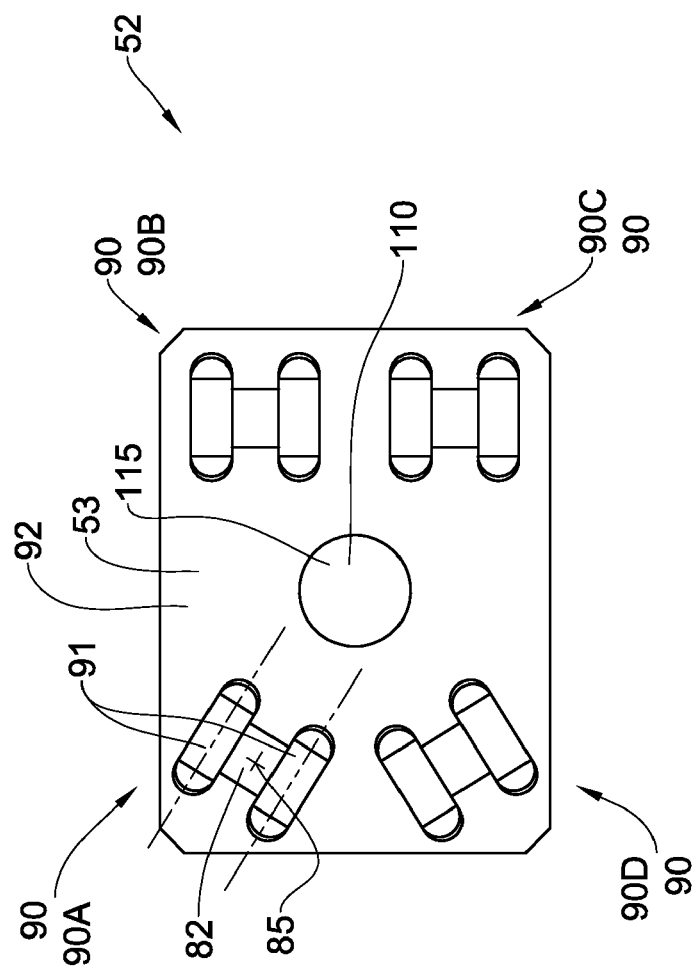
FIG. 6(b)
FIG. 6(a)

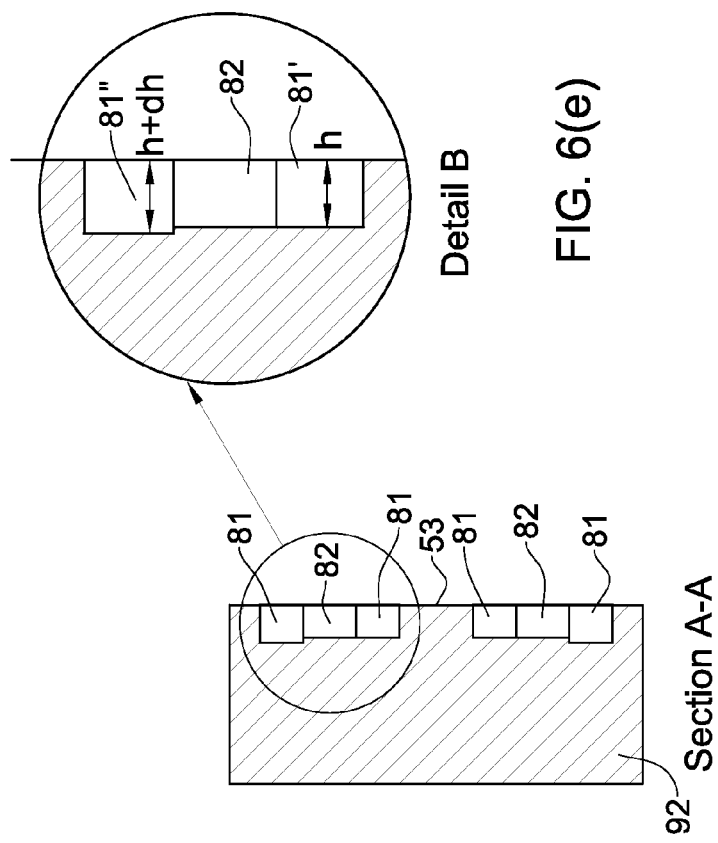
FIG. 6(e)
FIG. 6(d)
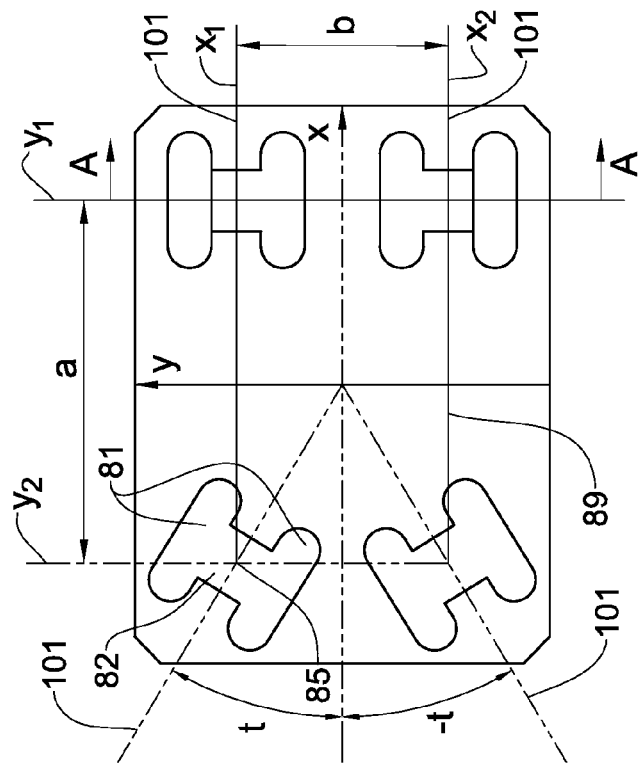
FIG. 6(c)

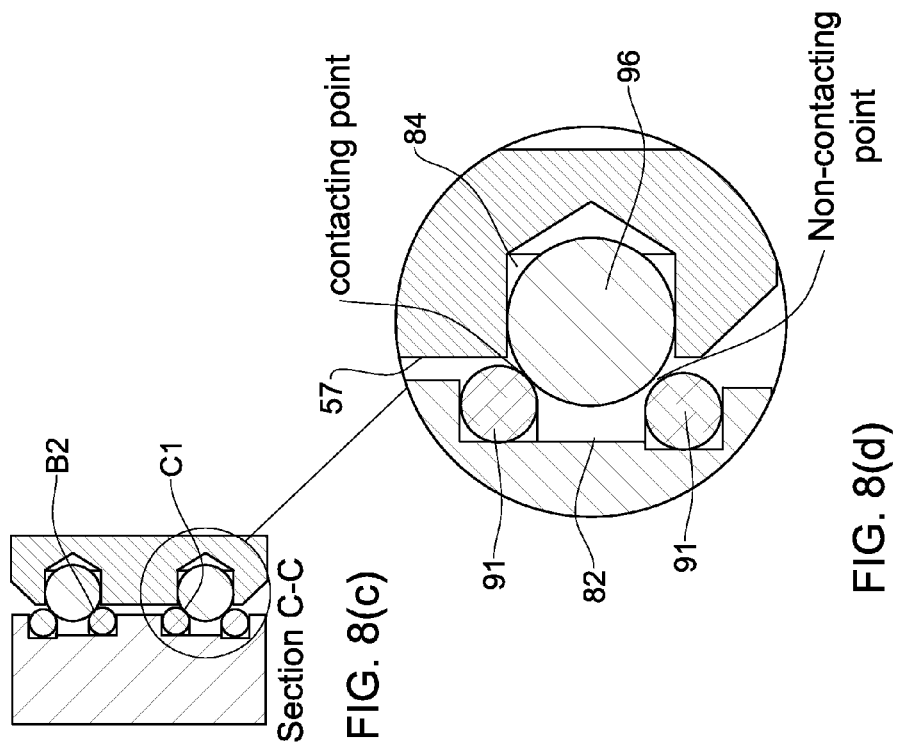
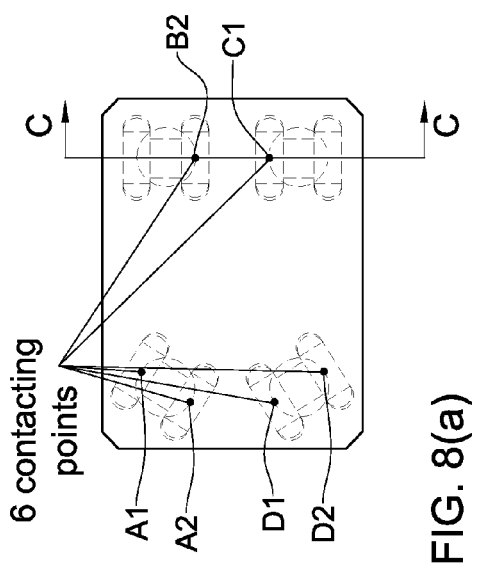
FIG. 8(a)
FIG. 8(b)
FIG. 8(c)
FIG. 8(d)

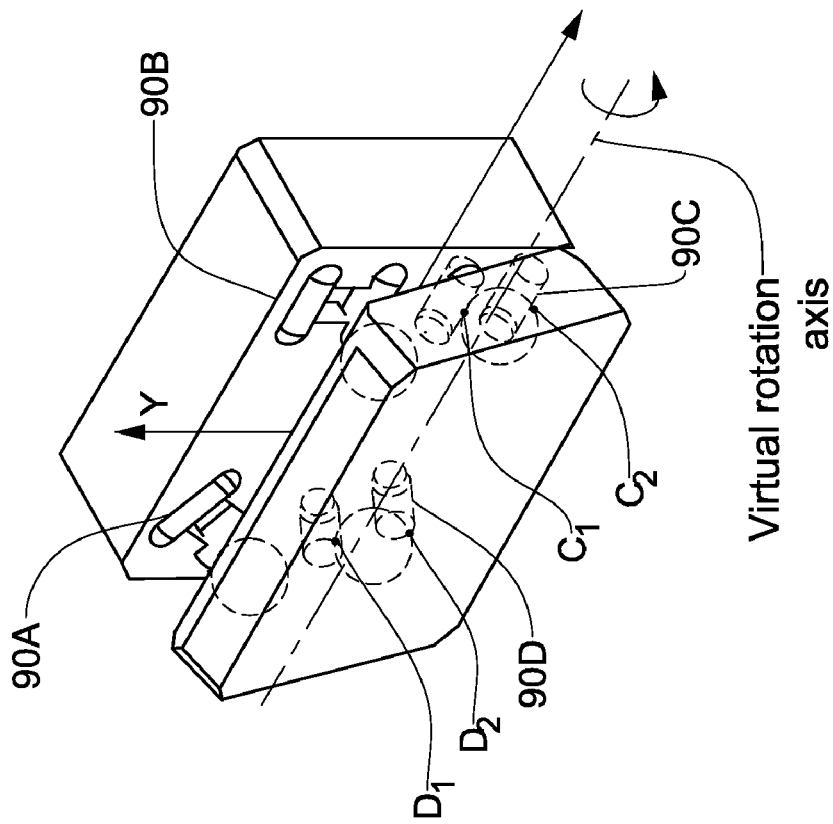
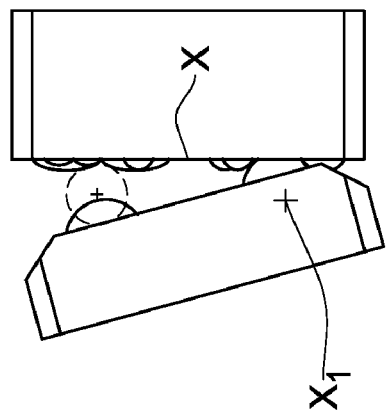
FIG. 9(b)
FIG. 9(a)

Section Q-Q

DENTAL ARTICULATOR

This application claims the benefit of prior U.S. provisional patent application No. 61/193,867 filed Dec. 31, 2008, the contents of which are hereby incorporated by reference in their entirety.

FIELD OF THE INVENTION

This invention relates to dental articulators.

BACKGROUND OF THE INVENTION

Dental articulators are well-known tools used by dental practitioners and technicians with dental models, in general for producing, developing or testing dental prostheses or dentures. Articulators are generally meant to provide a relative spatial relationship between the upper and lower jaws, often providing the user with valuable occlusal information, and are hinged to enable the upper and lower dental models to rotate with respect to one another, in a manner that may be analogous to that of a real jaw.

Simple dental articulators allow relative movement between the upper and lower dental models with one degree of freedom only, about the hinge axis, and often the dental models, which are typically made from plaster, are connected to the articulator in a manner that may cause damage to the models when removed therefrom. Extremely complex articulators are also known, which can imitate the occlusal and masticatory movement of a particular patient, but operation of such articulators is complex and may require specialist training.

There are also a range of articulators which provide relative movement between the upper and lower models, in degrees of freedom additional to rotation about the pivot axis of the articulator. Typically, the prior art articulators attempt to locate the pivoting axis at a position corresponding to the condyle.

US 2006/188838 discloses a dental articulator for connecting first and second dental models, and generally includes upper and lower arms hinging at their rear ends by a hinge. Each arm front end is connected by a coupling to a dental model. Each coupling generally includes a ball, a coupling, a rear socket and a fastener joining the coupling and rear socket such that the socket is movable rotationally, up and down, and side to side on the ball to a selected position. The hinge also provides for movements of the arms mimicking those of a human jaw. The lower arm means for adjusting the height of the hinge. Upper and lower dental models each include a holder of an incisor spacing assembly co-cast into the base. The holders hold an incisor pin for adjusting the vertical spacing between the fronts of the dental models.

US 2006/204921 discloses a dental articulator capable of finely adjusting a three-dimensional articulation posture and exerting a secure fastening force by means of a lever is provided. The dental articulator includes: a lower grip plate on which a lower mouth mold is mounted; a column disposed at one end of the lower grip plate; an arm having one end rotatably disposed at upper end of the column; and an upper grip plate disposed at the other end of the arm, wherein a first ball having a shape of sphere is disposed at the other end of the arm, and a second ball having a shape of sphere is disposed at a neck portion erected at a center of the upper grip plate, and wherein the dental articulator further comprises: a first clamp block having spherical recesses spherically contacting with the first and second balls, wherein a screw hole is provided at a central portion of the first clamp block; a second clamp block having spherical recesses spherically contacting with the first and second balls, wherein an engaging bolt hole is provided at a central portion of the second clamp block; a lever disposed on an outer surface of the second clamp block, wherein screw holes are provided to both ends of the lever, wherein an engaging bolt hole is provided to a central portion of the lever; an engaging bolt passing through the engaging bolt hole of the lever and the engaging bolt hole of the second clamp block to be engaged into the screw hole of the first clamp block; and fastening bolts engaged into the screw holes of the lever to shorten a distance between the first and second clamp blocks based on the engagement position.

US 2005/282105 discloses a dental articulator for connecting upper and lower dental models made from dental impressions of teeth and for moving the mandible in opening and closing, protrusive and lateral motions generally comprises upper and lower arms each having a front end for attachment respectively to upper or lower model. The upper arm includes a pair of condylar slots for receiving journals of the lower arm such that the lower arm may perform the opening and closing motion, the protrusive movement, and lateral movement of the mandible. A cantilever spring attached to the upper arm biases the journals toward the centric occlusion position. Slot stops limit protrusive movement and axle stops limit lateral movement.

U.S. Pat. No. 5,385,470 discloses an articulator for simulating jaw movements comprising an upper and a lower part for carrying an upper-jaw and/or lower-jaw model and connected by joints permitting one or more swiveling and linear motions, in which in the joint the lower part is guided relative to the upper part in one or more directions comprising components of motion in the cranial and/or dorsal direction and corresponding to surtrusion and/or retrusion.

SUMMARY OF THE INVENTION

According to a first aspect of the invention, there is provided a dental articulator comprising a first arm hingedly joined to a second arm about a pivot axis, each said arm adapted for mounting a dental model thereto, wherein at least one said arm comprises a bracket member adapted for mounting the respective dental model thereto, a base member adapted for being hingedly joined to the other said arm about said pivot axis, and a magnetic coupling arrangement configured for magnetically affixing the bracket member to the base member.

The articulator comprises a model mounting arrangement configured for enabling the dental model to be releasably mounted to said bracket member, and said model mounting arrangement is different from said magnetic coupling arrangement. The model mounting arrangement is spaced from the magnetic coupling arrangement in a direction substantially different from the direction in which the model is mounted to the model mounting arrangement.

The coupling arrangement is comprised in a mount, which is configured for providing a stable and repeatable relative positioning between the bracket member and the base member in a datum alignment position, while permitting relative movement therebetween in at least two degrees of freedom, for example including two rotational degrees of freedom different from rotation about the pivot axis.

The mount having a first mount part comprised in the base member and a second mount part comprised in the bracket member, and wherein the mount is configured for selectively providing, at least during operation of the articulator, for relative movement between the respective bracket member and the respective base member with respect to a datum alignment position.

The first mount part and second mount part are configured for defining a discrete plurality of contact points therebetween in said datum alignment position, and wherein selective portions of said contact points are disengaged from mutual contact for providing said relative movement. For example, there may be provided a first set of at least four said contact points at said datum alignment position, and a second set of at least four said contact points when carrying out a respective said relative movement. At least some of said contact points in said first set may also be included in said second set. Furthermore, at least some the contact points of said first set may be configured for preventing translational movement in one or two degrees of freedom between the first mount part and the second mount part in said datum alignment position.

In at least some embodiments, four contact points are provided for enabling rotation about each of two lateral axes and for enabling rotation about each of two transverse axes, though in each case at least some of the contact points may be different from those of other cases. The lateral axes are substantially parallel to the pivot axis while the transverse axes are substantially orthogonal to the pivot axis.

In some embodiments, each said contact point is provided between a generally hemispherical projection in one of said first and second mount parts, and a generally cylindrical projection in the other one of said first and second mount parts.

Each one of said first arm and said second arm may comprise a respective said bracket member adapted for mounting a respective dental model thereto, a respective said base member adapted for being hingedly joined to the other said arm about said pivot axis, and a respective said magnetic coupling arrangement configured for magnetically affixing the respective said bracket member to the respective said base member.

According to a second aspect of the invention there is provided a dental articulator comprising a first arm hingedly joined to a second arm about a pivot axis, each said arm adapted for mounting a dental model thereto, wherein at least one said arm comprises a bracket member adapted for mounting the respective dental model thereto, a base member adapted for being hingedly joined to the other said arm about said pivot axis, and a mount having a first mount part comprised in the base member and a second mount part comprised in the bracket member, wherein the mount is configured for selectively providing, at least during operation of the articulator, for relative movement between the respective bracket member and the respective base member with respect to a datum alignment position, and further comprising a coupling arrangement configured for coupling the bracket member to the base member to allow for said relative movement in response to a suitable external force or couple while urging said first mount part into abutting contact with said second mount part to assume said datum alignment position in the absence of the external force or couple.

The articulator may comprise one or more features according to the first aspect of the invention, mutatis mutandis. For example, the coupling arrangement may be a magnetic coupling arrangement configured for magnetically attracting the bracket member the base member with respect to one another.

The articulator may comprise a model mounting arrangement configured for enabling the dental model to be mounted to said bracket member, wherein said model mounting arrangement is different from said magnetic coupling arrangement.

The said mount is configured for providing a stable and repeatable relative positioning between the first mount part and the second mount part in said datum alignment position, while permitting relative movement therebetween in at least two degrees of freedom, for example including two rotational degrees of freedom.

The first mount part and second mount part may be configured for defining a discrete plurality of contact points therebetween in said datum alignment position, and wherein selective portions of said contact points are disengaged from mutual contact for providing said relative movement, for example as disclosed for the first aspect of the invention, mutatis mutandis.

The coupling arrangement may instead comprises a resilient element configured for elastically affixing the bracket member to the base member. For example, the resilient element may comprise a coil spring anchored at one longitudinal end thereof to said base member and at another longitudinal end thereof to said bracket member.

The bracket member may comprise a mounting arrangement adapted for reversibly mounting a dental model thereto. the mounting arrangement may comprise at least one projecting element cantilevered from said bracket member and adapted for reversible engagement with respect to a corresponding aperture provided in said dental model, wherein said at least one projecting element and said corresponding aperture are suitably located such as to provide a desired relative position between said dental model and said pivot axis, at least in said datum position. The projecting element may comprise a radially deformable free end, said free end having a datum dimension larger than a corresponding internal dimension of said aperture, and being radially deformable from said datum dimension to be at least temporarily accommodated inn said aperture when said model is mounted to said bracket member. At least one projecting element is configured such that when said model is mounted thereto, said free end passes through said corresponding aperture and at least partially restores said datum dimension. At least one projecting element comprises a plurality of longitudinal resilient elements circumferentially arranged with respect to a base connected to said bracket member.

At least one said arm may comprise a mechanical stop arrangement to limit pivotal movement of said arms toward one another about said pivot axis.

In at least some embodiments, the two arms may be substantially identical one with respect to another.

According to a third aspect of the invention, there is provided a dental articulator comprising a first arm hingedly joined to a second arm about a pivot axis, each said arm adapted for mounting a dental model thereto, wherein at least one said arm comprises a bracket member adapted for mounting a dental model thereto, articulated with respect to a base member that is adapted for being hingedly joined to the other said arm about said pivot axis, allowing independent movement of the dental model with respect to the pivot axis hingedly linking the arms during operation of the articulator.

The articulator according to the third aspect of the invention may comprise one or more features according to the first aspect of the invention, one or more features according to the second aspect of the invention, mutatis mutandis.

According to a fourth aspect of the invention, there is provided a dental articulator comprising a first arm hingedly joined to a second arm about a pivot axis, each said arm adapted for mounting a dental model thereto, wherein at least one said arm comprises a bracket member adapted for mounting the respective dental model thereto, a base member adapted for being hingedly joined to the other said arm about said pivot axis, and a mount configured for kinematically coupling the respective bracket member and the respective base member. Such kinematic coupling allows for relative movement between the bracket member and the base member in response to a suitable external force or couple while urging the bracket member into abutting contact with base member to assume a datum alignment position in the absence of the external force or couple.

The articulator according to the fourth aspect of the invention may comprise one or more features according to one or more of the first aspect of the invention, and/or of the second aspect of the invention, and/or of the third aspect of the invention, mutatis mutandis.

Herein, by "operation" of the articulator is meant utilization of the articulator after the relative position between the arms and the corresponding dental models has been set up, and includes inducing relative motion between the opposed dental models via the articulator, such as for example to simulate mastication or other movements of the teeth. Thus, the term "operation" with respect to the articulator excludes activities such as alignment and fitting/mounting of the dental models to the articulator.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3 illustrates, in top/front view, the embodiment of FIG. 1 without the teeth models.

FIG. 4 illustrates, in side view, the embodiment of FIG. 1 with the arms in the closed position.

FIGS. 6(a) to 6(e) illustrate various views, sections and details of a first mount part of the embodiment of FIG. 1.

FIGS. 8(a) to 8(d) illustrate various views, sections and details of the mount of the embodiment of FIG. 1.

FIGS. 9(a) to 9(b) illustrate various views, of the mount part of the embodiment of FIG. 1 in one operational mode.

FIG. 13(a) when the mount is in the a datum alignment position; FIG. 13(b) when providing a transverse rotation about lateral axis x1; FIG. 13(c) when providing a lateral rotation about transverse axis y1.

DETAILED DESCRIPTION OF EMBODIMENTS

Figure 1:
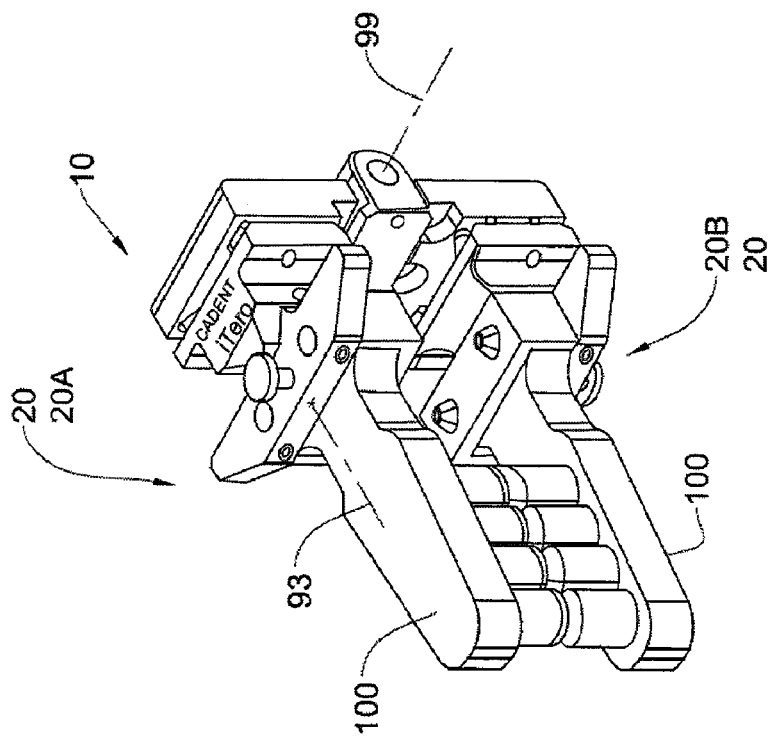
FIG. 1 illustrates, in top/front isometric view, an embodiment of the invention and teeth models mounted thereto.

Referring to FIGS. 1 to 5, a dental articulator according to an embodiment of the invention is illustrated. The articulator, generally designated with the reference numeral 10, comprises an upper arm 20A and a lower arm 20B hingedly joined together with respect to pivot axis 99. In this embodiment, the upper arm 20A and the lower arm 20B are modular units, substantially identical to one another in form and structure, which simplifies manufacture, repair and logistics, for example. For the sake of simplifying the description of the upper arm 20A and the lower arm 20B, these are also collectively or individually referred to as arm 20 or arms 20.

Figure 2:
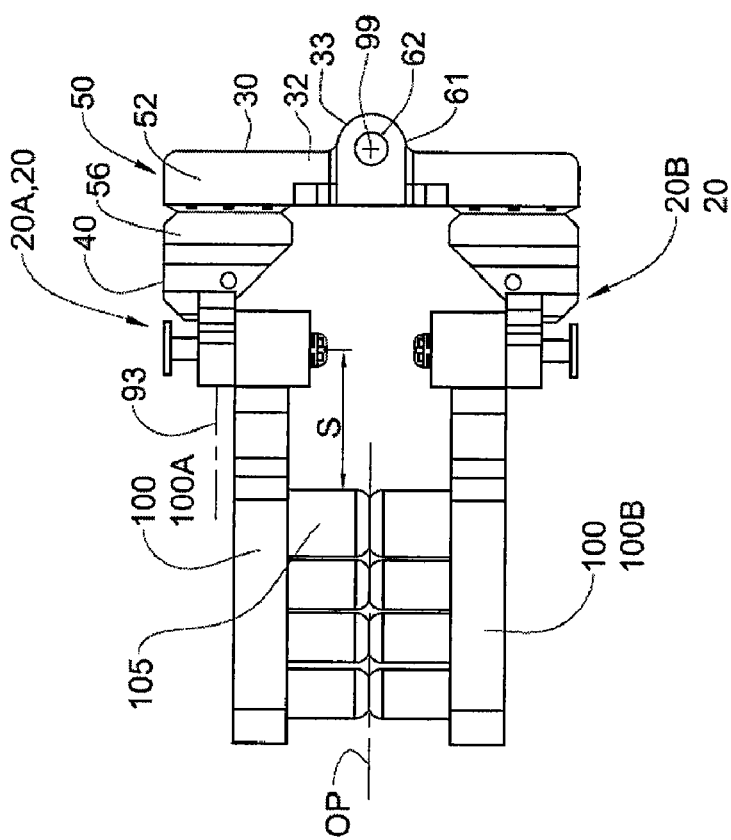
FIG. 2 illustrates, in side view, the embodiment of FIG. 1.

Referring in particular to FIG. 2, each arm 20 comprises a generally L-shaped form when viewed from the side, i.e., along axis 99, the arms of the L comprising base member 30 and a mounting bracket 40 mounted thereto via dynamic mount 50, which comprises a first mount part 52 and a second mount part 56. As will become clearer below, the mounting bracket 40 is configured for mounting a respective tooth model 100 thereto in operation of the articulator. The bracket 40 defines a longitudinal axis 93 substantially parallel to the occlusal plane OP of the corresponding tooth model 100 and orthogonal to the pivot axis 99.

Referring in particular to FIGS. 2 and 3, the base member 30 comprises a hinge end 32, having a hinge element 31 at one end thereof, and first mount part 52 at another end 34 thereof. Hinge element 31 of each arm 20 is pivotably mounted to a common hinge base 61 with respect to axis 99, and each hinge element 31 comprises a plurality of hinge loops, spaced to allow the hinge loops of the other arm to be coaxially aligned therewith, and which cooperate with a pivot pin 62 of hinge base 61, allowing pivoting of each arm 20 with respect to the hinge base 61. Hinge base 61 comprises raised sections 63 comprising pivot stops 64, which limit the pivoting range of the arms 20 to the fully closed position illustrated in FIGS. 1 to 4, wherein respective counter-stops 33 provided in base member 30 abut against the pivot stops 64. The pivot stops 64, are thus configured for limiting the relative rotation of the arms 20A, 20B towards each other such to prevent the respective teeth models 100 (when these are mounted to the arms 20A, 20B, respectively) being pressed against each other with undue force or beyond the occlusal plane. Thus, the hinge base 61 allows the teeth models to mutually touch at the occlusal plane, but prevents further rotation of the arms 20A, 20B towards one another, while permitting rotation away from one another (FIG. 5).

Figure 5:
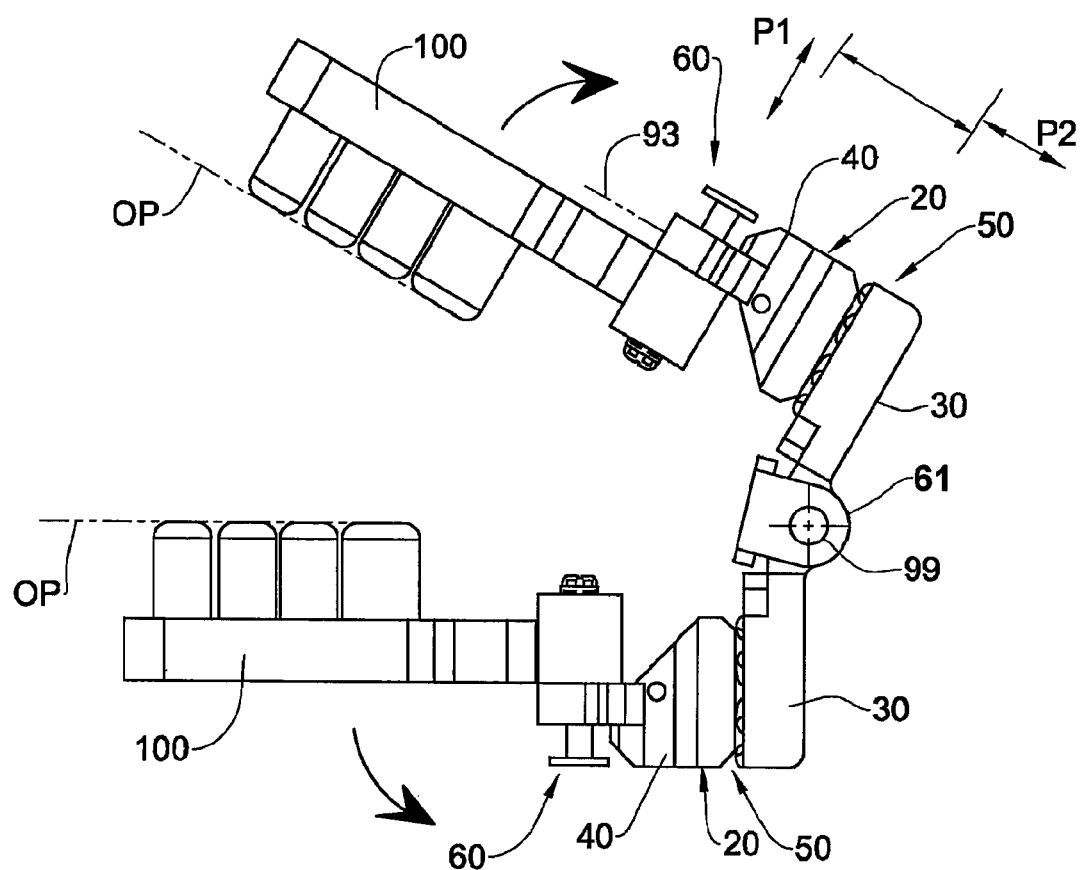
FIG. 5 illustrates, in side view, the embodiment of FIG. 1 with the arms in the open position.
Figure 7C:
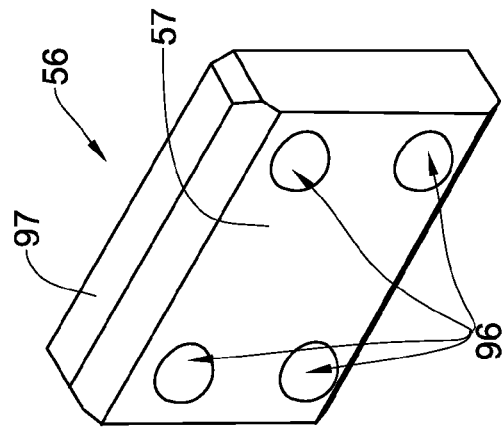
FIGS. 7(a) to 7(c) illustrate various views, of a second mount part of the embodiment of FIG. 1.
Figure 7B:
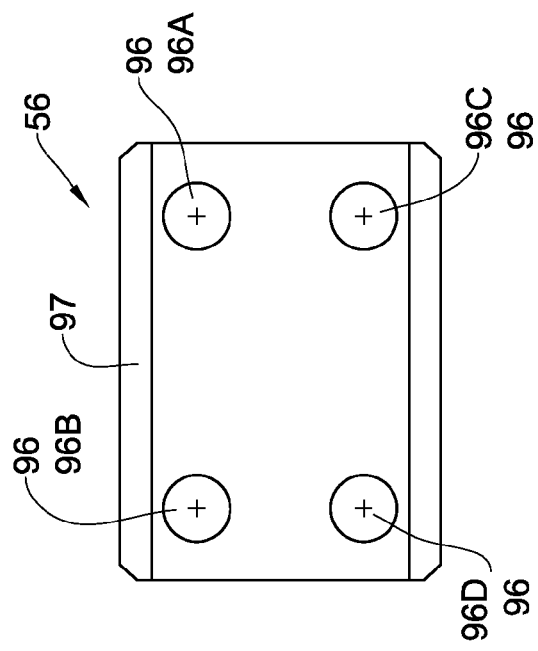
Figure 7A:
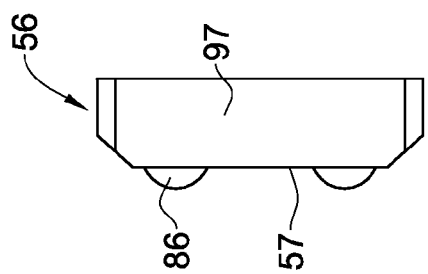

As best seen in FIG. 5, the hinge elements 31 are coupled to one another and/or to the hinge base 61 such that the two base members 30 pivot away from or towards the hinge base 61 in a synchronized manner, i.e., pivot through concurrently nominally equal angular displacements. In variations of this embodiment, the hinge arrangement between the upper and lower arms 20 may be such as to enable each arm to independently pivot with respect to hinge base 61.

Referring in particular to FIG. 3, the mounting bracket 40 has a generally T-shaped plan form (when viewed from above), comprising at the base 42 of the T the second mount part 56, and at the bar 44 of the T a model mounting arrangement 60. As may be seen also in FIG. 5, the model mounting arrangement 60 is displaced from the mount 50 in a direction along the axis 93, i.e., generally parallel to the occlusal plane Op of the respective tooth model 100, and generally orthogonal to the pivot axis 99.

The dynamic mount 50, which dynamically joins together the respective bracket 40 and base member 30, is configured for permitting at least limited relative motion between the bracket 40 and base member 30 in at least two rotational degrees of freedom, independently of any pivoting motion about axis 99: rotation about axes parallel to the pivot axis 99 (and thus parallel to the condyle axis), and rotation about axes orthogonal thereto and to the respective longitudinal axis 93. The dynamic mount 50 is also configured for repeatably enabling the first mount part 52 and the second mount part 56 to assume a datum aligned relationship (also referred to interchangeably herein as a datum alignment relationship or datum alignment position), illustrated in FIGS. 1 to 5, FIGS. 8(*a*) to 8(*d*), in which the teeth models 100 are aligned in their occlusal positions when mounted to the respective arms 20A, 20B.

Referring to FIGS. 6(*a*) to 6(*e*), the first mount part 52 comprises four substantially identical pairs of pins 90A, 90B, 90C, 90D (for ease of reference the pin pairs will also be referred to herein individually or collectively by the numeral 90) mounted in a base element 92. Each pin pair 90 comprises two substantially identical cylindrical pins 91, which are received in respective laterally spaced parallel recesses 81 formed on an outer-facing face 53 of first mount part 52. Between each pair of recesses 81 there is a cavity 82, defining a geometric center 85 associated with the respective pin pair 90. For each pin pair 90, the respective pins 91 have their longitudinal axes parallel to one another, and furthermore, part of the cylindrical surface 93 of each pin projects beyond face 53. A pin pair axis 101 can be defined for each pin pair 90 as being parallel to the longitudinal axes of the respective pins 91 and passing through the respective geometric center 85. Axis 101 may be coplanar with face 53, for example.

Referring to FIG. 6(*c*), the centers 85 of the four pin pairs 90 lie on the four corners of an imaginary rectangle 89 projected on face 53, centrally aligned on lateral axis x (parallel to axis 99) and transverse axis y, orthogonal thereto, defined on face 53. Thus, laterally adjacent pin pairs 90A, 90B are laterally spaced by dimension a, and transversely adjacent pin pairs 90A, 90D are transversely spaced by dimension b, and similarly, laterally adjacent pin pairs 90C, 90D are laterally spaced by dimension a, and transversely adjacent pin pairs 90B, 90C are transversely spaced by dimension b. Furthermore, pin pairs 90B and 90C are arranged with their pin pair axes 101 parallel to one another, while the pin pair axis 101 of pin pair 90A is in diverging relationship with respect to the pin pair axis of pin pair 90D, at angle ±t to the lateral axis x. In one example, dimension a may be about 1.6 cm, dimension b may be about 0.9 cm and angle t may be about ±30 degrees. Referring to FIGS. 6(*d*), 6(*e*), each pair of respective recesses 81 for pin pair 90B and 90C comprises an inward-lying recess 81' having a depth h, and an outward-lying recess 81" having a deeper depth, h+Δh. This results for each pin pair 90B, 90C, in the respective pin that is received in recess 81" being more imbedded with respect to face 53 than the respective pin that is received in recess 81'. The respective recesses 81 for pin pairs 90A and 90D uniformly have a depth of h.

The pins 91 are glued, bonded, press-fitted or otherwise permanently received in their respective recesses 81, at least during operation and use of the articulator 10.

In alternative variations of this embodiment, the first mount part 52 may be integrally formed, cast, or machined from a blank, rather than made from several components mounted together.

Second mount part 56 comprises four substantially identical spherical balls 96A, 96B, 96C, 96D (for ease of reference the balls will also be referred to collectively or individually by the numeral 96) mounted in a base element 97. Each ball 96 is received in respective laterally spaced parallel recesses 84 (FIG. 8(*d*)) formed on an outer-facing face 57 of second mount part 56, in positions corresponding to those of the centers 85 of the first mount part 52 when the face 53 thereof is facing face 57 of the second mount part 56, each ball 96 having a hemispherical surface 86 projecting beyond face 57 (FIG. 8(*a*)).

Thus, when the first mount part 52 and the second mount part 56 are in the aforesaid datum alignment relationship (FIGS. 1 to 5, 8(*a*) to 8(*d*)), the hemispherical surface 86 of each ball 96A, 96B, 96C, 96D are aligned with the respective geometric centers 85 of the pin pair 90A, 90B, 90C, 90D, respectively. Furthermore, and referring to FIGS. 8(*a*), 8(*c*) and 8(*d*) in particular, in the datum alignment relationship the balls 96 are in abutting contact with the respective pin pairs 90 at six contact points: two contact points A1, A2, between ball 96A and pin pair 90A; two contact points D1, D2 between ball 96D and pin pair 90D; one contact point B2 between ball 96B and pin pair 90B; and one contact point C1 between ball 96C and pin pair 90C. The last two contact points B2, C1 are with respect to the inner facing pins 91 of each pin pair, and the outer facing pins 92 of the pin pairs 90B and 90C do not make contact with the respective balls 96B, 96C, in the datum alignment relationship since they are further recessed into the base element 92 on account of their deeper respective recesses 81" (see also FIG. 6(*e*)).

The six contact points fix the spatial position of the first mount part 52 with respect to the second mount part 56 in a repeatable manner, i.e., whenever the two mount parts are separated in any manner one from the other they will return to the same datum alignment relationship when brought together again. The six contact points are arranged in such a manner that does not permit relative translations between the first mount part 52 and the second mount part 56 along the x or y axes when in the datum alignment relationship. Relative movement orthogonal to the x and y axis at the datum alignment relationship is prevented by means of coupling arrangement 110, which maintains the two mount parts 52, 56 are held in an abutting contact configuration. Thus, mount 50 operates in a manner similar to a kinematic mount.

In addition to providing a repeatable datum alignment relationship, the dynamic mount 50 is also configured for allowing the second mount part 56 to rotate with respect to the first mount part 52 (and thus allowing rotation of the respective tooth model 100 when mounted to the respective bracket 40 with respect to the respective base element 30) about a virtual or pivot axis parallel to lateral axis x and/or about a virtual or pivot axis parallel to transverse axis y, while the two mount parts 52, 56 are held in a different abutting contact configuration by means of coupling arrangement 110.

Transverse rotation, i.e. rotation about an axis parallel to lateral axis x (and thus parallel to pivot axis 99), may be accomplished in two ways for each mount 50. In a first such rotation, referred to herein as a positive transverse rotation and referring to FIGS. 9(*a*) and 9(*b*) in particular, balls 96A and 96B are spaced from respective pin pairs 90A and 90B. This is accomplished by rotating the second part 56 about a virtual lateral rotation axis x1 substantially parallel to lateral axis x, in which ball 96D remains in abutting contact with pin pair 90D at contact points D1, D2, and ball 96C has a second contact point C2 with pin pair 90C in addition to remaining also in contact at C1.

Because the outer facing pin of pin pair 90C is further recessed than the inner facing pin or the pins of pin pair 90D, axis x1 will be slightly diverging with respect to axis x, but since Δh is small compared to the depth h of the recesses and spacing a, the axis x1 may be regarded as nominally parallel to axis x.

Virtual axis x1 connects the centers of the balls 96C, 96D when these are in abutting contact with their respective pin pairs. In the second such rotation, referred to herein as a negative transverse rotation, and referring to FIG. 6(*c*), the second part 56 is rotated about a second virtual lateral rotation axis x2, also nominally parallel to lateral axis x, in which balls 96A and 96B are in abutting contact with pin pairs 90A and 90A, respectively, at two respective pairs of contact points A1, A2 and B1, B2 (which includes a second contact point B1 between the further recessed pin of pin pair 90B and ball 96B), and balls 96C and 96D are spaced from respective pin pairs 90C and 90D. Virtual axis x2 connects the centers of the balls 96A, 96B when these are in abutting contact with their respective pin pairs.

Thus, while rotating the second mount part 56 about virtual axis x1 or x2, the second mount part 56 is in contact with the first mount part 52 at four contact points, which provides for stability of the position of the virtual axes. (It is to be noted that in the aforesaid rotations about x1 or x2, the respective 4 contact points in each case are not static, but change with respect to the position of the respective contact points on the respective balls 96, as the respective pairs of balls slidingly rotate over the respective pin pairs.) Moreover, by having the respective axes 101 of pin pair 90A and 90D non parallel to the respective axes 101 of pin pairs 90B and 90C, respectively, translation of the first mount part 52 with respect to the second mount part 56 is prevented in the lateral direction, while the contact configurations prevents corresponding translations in the transverse direction.

In a similar manner, mutatis mutandis, and referring to FIG. 6(c), the mount 50 allows for lateral rotation, i.e. rotation about an axis parallel to transverse axis y (and thus orthogonal to pivot axis 99 and to the occlusal plane when the arms 20 are in the occlusal position). In a first such rotation, referred to herein as a positive lateral rotation, balls 96A and 96D are spaced from respective pin pairs 90A and 90D by rotating the second part 56 about a virtual transverse rotation axis y1 substantially parallel to lateral axis y, in which balls 96B and 96C are in abutting contact with pin pairs 90B and 90C, respectively, at one contact point each B2, C1, i.e., with respect to the inward facing, raised respective pin. Virtual axis y1 connects the centers of the balls 96B, 96C when these are in abutting contact with their respective pin pairs. In the second such rotation, referred to herein as a negative lateral rotation, the second part 56 is rotated about a second virtual transverse rotation axis y2, also substantially parallel to lateral axis y, in which balls 96A and 96D are in abutting contact with pin pairs 90A and 90D, respectively, at two respective pairs of contact points, A1, A2 and B1 B2, and balls 96B and 96C are spaced from respective pin pairs 90B and 90C. Virtual axis y2 connects the centers of the balls 96A, 96D when these are in abutting contact with their respective pin pairs.

Thus, while rotating the second mount part 56 about virtual axis y1 or y2, the second mount part 56 is in contact with the first mount part 52 at two contact points and four contact points, respectively, which provides for stability of the position of the virtual axes. Moreover, by having the respective axis 101 of pin pair 90A non parallel to the respective axis 101 of pin pair 90D, respectively, translation of the first mount part 52 with respect to the second mount part 56 is prevented in the lateral direction when rotating about axis y1. On the other hand, rotation about axis y2 may be accompanied by lateral relative translation between the mount parts 52, 56. The contact configurations prevent corresponding translations in the lateral direction when rotating in the positive or negative transverse directions, which provides another degree of freedom to mount 50.

In alternative variations of this embodiment, the first mount part 52 may comprise the pin pair arrangement while the second mount part 56 comprises the ball arrangement, for example, the first mount part 52 may be comprised in the mounting bracket 40, and the second mount part 54 in the base 30.

In yet other alternative variations of this embodiment, the first mount part 52 may comprise part of the pin pair arrangement and part of the ball arrangement, while the second mount part 56 comprises the corresponding parts of the ball arrangement and the pin arrangement.

In yet other alternative variations of this embodiment, the first mount part 52 may comprise any suitable pin pair arrangement while the second mount part 56 comprises any suitable and corresponding ball arrangement. In one such example three balls may be provided on one mount part, with three pin pairs on the other mount part.

Figure 11:
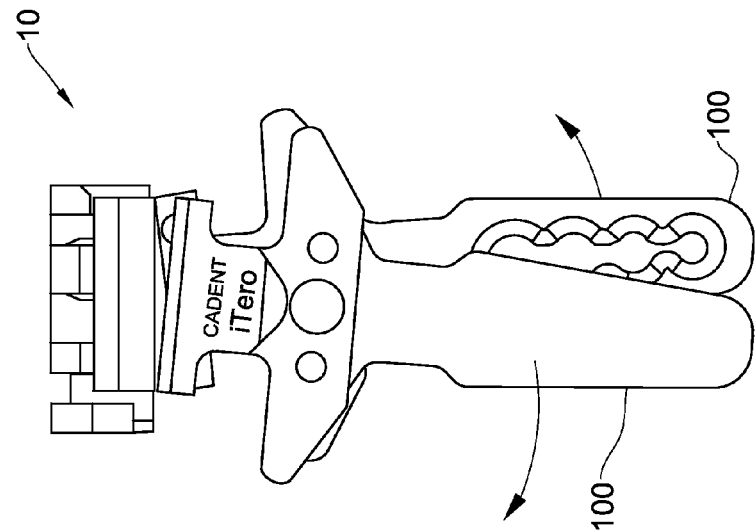
FIG. 11 illustrates in top view the embodiment of FIG. 1 in the mode of operation of FIG. 10.
Figure 12:
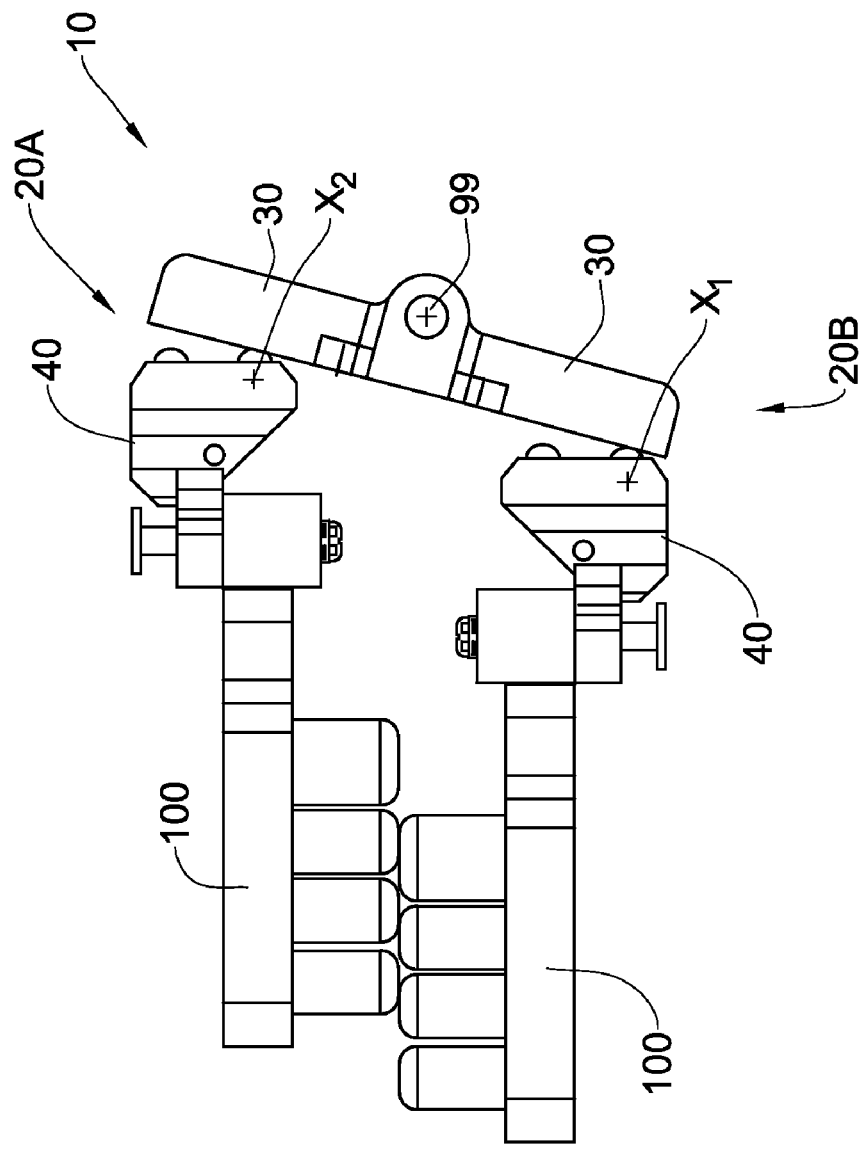
FIG. 12 illustrates in side view the embodiment of FIG. 1 in another mode of operation.
Figure 13A:
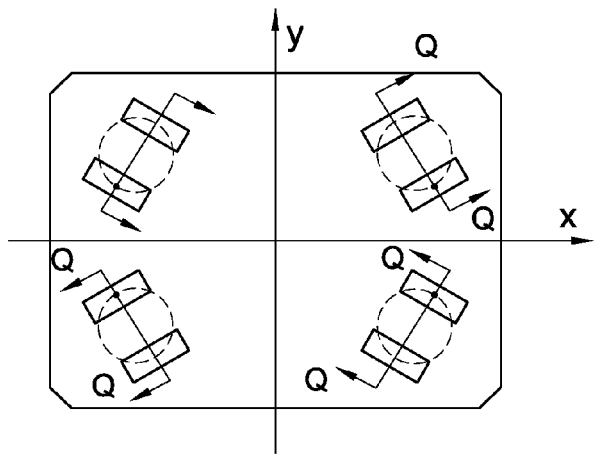
FIGS. 13(a) to 13(c) illustrate a variation of the embodiment of FIGS. 1 to 12, indicating contact points.
Figure 14:
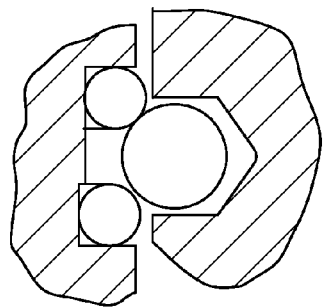
FIG. 14 illustrates in partial view section Q-Q of FIG. 13(a).
Figure 13B:
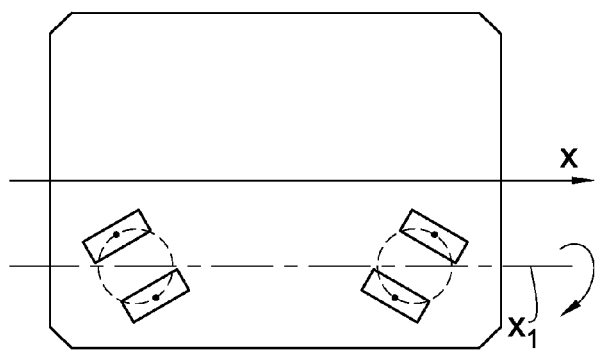
Figure 13C:
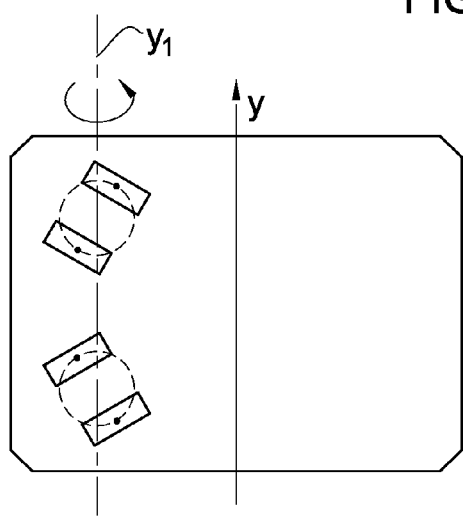

In another variation of this embodiment, and referring to FIGS. 13(a) to 13(c) and to FIG. 14, four pairs of balls and four corresponding pin pairs are provided, in rectangular configuration, for example similar to the embodiment of FIGS. 1 to 12, mutatis mutandis, but each adjacent pin pair in the mount having their respective pin pair axes diverging (or alternatively, converging, or alternatively each adjacent pin pair having their respective pin pair axes non-parallel with respect to one another) with respect to one another. Further, for example, for each such pin pair, one pin is further recessed than the other pin, so that in the datum alignment position (FIG. 13(a)), the balls rest on only 4 contact points, for example the inner facing pin closes to the x-axis (FIG. 14). In such a configuration, the first mount part is in contact with the second mount part at four contact points also when pivoting about virtual axes x1, y1 parallel to axis x or axis y, respectively, as the respective pair of balls about which pivoting is being carried out is in sliding abutting contact with the two respective pin pairs at two contact points each (FIGS. 13(b), 13(c)).

At the same time, the mutually divergent relationship between each adjacent pair of pin pairs restricts any displacement in the x or y directions.

In yet other alternative variations of this embodiment, the first mount part 52 and the second mount part 56 comprises any suitable floating pivot arrangement that allows lateral and transverse pivoting of one mount part with respect to the other mount part, with respect to each one of two laterally spaced transverse axes and with respect to each one of two transversely spaced lateral axes, respectively.

While in the illustrated embodiment the faces 53 and 57 are substantially planar and substantially orthogonal to the longitudinal axis 93 of the bracket 40, in alternative variations of this embodiment, these faces may be at planes at any desired angle to axis 93, or may comprise any suitable profile, for example concave/convex.

As mentioned earlier, the mount 50 further comprises a magnetic coupling arrangement 110 for providing a restoring force in direction P2 (FIG. 5) that urges together the base member 30 and bracket 40, while at the same time allowing for the aforesaid manual manipulation of the bracket 40 with respect to base member 30 maintaining the particular contact between specific balls 96 and pin pairs 90 required for the particular lateral or transverse rotation. During such manipulation, the coupling arrangement 110 provides a couple about the rotational axis about which the first and second mount parts are being rotated with respect to one another. Direction P2 is generally parallel to axis 93 in this embodiment. The coupling arrangement 110 comprises a permanent magnet 115 received in a recess (not shown), centrally located with respect to the four pin pairs 90 on face 53, and which magnetically cooperates with face 57 of second mount part 56, which is made of a material, or comprises an element made of a material, that is magnetically attracted by a magnet, for example a magnetically attracted metal such as iron. In alternative variations of this embodiment, the second mount part 56 also comprises a permanent magnet, having an opposite pole facing the exposed pole of magnet 115. In yet other alternative variations of this embodiment, the second mount part 56 also comprises a magnet, while the first mount part 52 made of a material that is magnetically attracted by a magnet.

The coupling arrangement 110 provides, via said manipulation, for at least some relative movement between the base member 30 and bracket 40, sufficiently for one or more of the balls 90 to fully clear their respective cavities 82, and thus allow the bracket 40 to be rotated with respect to the base member 30 a number of different axes while maintaining contact between other balls 90 and the first mount part 52.

In alternative variations of this embodiment, the coupling arrangement 110 may be replaced instead with any suitable coupling arrangement, including for example a dynamic or flexible connector, such as for example an articulated joint, universal joint, an elastic element, a spring or plurality of springs and so on connected to the bracket 40 and to the base member 30. For example, in the case of an elastic element or spring(s), the coupling arrangement may have an unstressed longitudinal axis substantially parallel or coaxial with a central longitudinal 93 axis of bracket 40, for example, and may be connected to bracket 40 and to base member 30 in a slightly stretched (elastically) and tensioned state, thus storing elastic potential energy, and may elastically stretch further to accommodate the relative movement between the mount parts, and enabling restoration of the latter to the datum aligned position.

In alternative variations of this embodiment, the base elements 30 of the two arms 20A and 20B may be integrally joined, for example via a film hinge arrangement.

The model mounting arrangement 60 is configured for enabling a dental model of part or the full dental arch (upper or lower) to be mounted thereonto. In the illustrated embodiment, such mounting is reversible, but in alternative variations of this embodiment the model mounting arrangement permanently mounts the dental models to the respective arms 20. In yet other alternative variations of this embodiment, the details of the mounting arrangement may vary according to the particular geometry of the dental model, in particular the engagement arrangement thereof, if any.

Referring to FIG. 5, in this embodiment, the model mounting arrangement 60 is configured for enabling the tooth model to be mounted thereto in a direction P1 that is generally orthogonal to the occlusal plane OP of the respective tooth model 100, which direction P1 is different from magnetic coupling direction P2. In this embodiment, directions P1 and P2 are substantially non-parallel, and generally orthogonal.

Referring in particular to FIGS. 2, 3, 4 and 10, the articulator 10 according to the illustrated embodiment is configured for use with dental models such as models 100A, 100B, also referred to collectively or separately as model 100, each of which may comprise a positive teeth representation of one or more teeth 105 or a full dental arch, formed on a base 120, and further comprising a mounting block 130 formed at one end of the corresponding model 100A, 100B that is in closest proximity to the relative position of the condyle joint of the real jaw. In this embodiment, each mounting block 130 is formed with a pair of laterally-spaced cylindrical apertures 135, which are longitudinally spaced along the respective model 100 at a particular spacing S with respect to the respective teeth representations 105, such as to provide a desired spatial relationship between the respective model 100 and pivot axis 99, when mounted to the articulator 10, representative of the spatial relationship between the respective real teeth and condyle axis of the patient. The models 100 may be made, for example, according to the teaching of U.S. Pat. No. 7,220,124, assigned to the present Assignee, and the contents of which are incorporated herein in their entirety.

For each teeth model 100, the respective teeth representations 105 include a number of teeth on one side of the jaw, representing a number of adjacent molars, for example. However, the teeth representation 105 may instead include a different set of teeth, for example a set of incisors, or half or a full dental arch, and in any case the teeth representation 110 may optionally contain one or more representations of a dental site, including one or more dental preparations in place of corresponding teeth, the preparations being for the purpose of fitting dental prostheses thereto.

The mounting arrangement 60 enables the model 100 to be mounted in a cantilevered manner from the bracket element 40, in particular from one end thereof that is axially opposed to the other end thereof that comprises the second mount part 56. The mounting arrangement 60 comprises a pair of transversely spaced, substantially parallel engagement snap fit prongs 70 that are configured for reversibly engaging with respect to the respective apertures 135 of the corresponding tooth model 100. Each prong 70 comprises a cylindrical base projects from abutment surface 48 of the bar 44 and a resilient portion, cantilevered from the base, and which comprises a plurality of (in this embodiment, four) elongate resilient elements circumferentially arranged with respect to the base and circumferentially spaced via longitudinal gaps. The elements each comprises a sloping portion that radially slopes towards the longitudinal axis 92 of the prong 70, and an enlarged portion at the free end of the prong 70 that radially projects further outwardly than the perimeter of base when the elements are in the datum, unstressed condition. The enlarged portion comprises a conical or rounded free end, a waist portion defining the radially outermost surfaces of enlarged portions, and an engaging shoulder adjacent the sloping portion. Thus, together the plurality of elements form a substantially frustoconical or pyramidal portion comprising the sloping portions, and a bulging portion (comprising the enlarged portions) having a rounded free end.

The external width or diameter of the prong base is just less than the internal width or diameter of the apertures 135, and each prong is configured for enabling the prong elements to be radially elastically deflected inwardly, such that the radially outermost surfaces of enlarged portions, i.e. defining the prong waist, are displaced from axis 92 by a distance substantially equal to the radius of the apertures 135.

The longitudinal length of the prong 70 is greater than the depth of aperture 135, and the latter is substantially similar to the sum of the longitudinal length of the base 72 together with the longitudinal length of the sloping portions of the prong 70 taken along axis 92. In alternative variations of this embodiment, though, the apertures 135 may be diverging or stepped, for example, or otherwise configured, for enabling the prongs 70 to be anchored within the corresponding apertures 135 via the restoring force generated onto the aperture walls by the prong elements.

To engage a tooth model 100 to the corresponding bracket 40, the mounting block 130 is brought into proximity with the bar 44 such that the prongs 70 are aligned with the apertures 135 of the model 100. The mounting block 130 is then pushed towards the abutment surface 48 so that the prongs 70 are received into the apertures 135. In doing so, the corresponding elements of the prongs 70 are elastically deformed, storing elastic potential energy, so as to enable the enlarged portions to pass through the aperture 135, this being facilitated via the rounded free ends. When the block 130 is in abutment with abutment surface 48, the enlarged portions fully clear the apertures 135 and spring back to the unstressed state, or closer thereto, by means of all or part of the elastic potential energy that was previously stored, and the shoulders engage against an outer surface of the block 130 around the mouth of apertures 135. The enlarged portions assume their non stressed configuration, or close thereto, wherein the radius of the waist portion now exceeds the internal radius of the apertures 135, locking the block 130, and thus the respective tooth model 100, in place.

In alternative variations of this embodiment, more than two prongs may be provided, mutatis mutandis, the tooth models 100 being correspondingly configured for being engaged thereto.

In yet other variations of this embodiment, a single prong may be provided, mutatis mutandis, and this may optionally be further configured for preventing relative rotation between the corresponding tooth model and the bracket 40 about the longitudinal axis of the prong, for example comprising a suitable circumferential stop arrangement or a non-axisymmetric cross-section, or alternatively for providing such movement as part of the said variable joint. Alternatively, a single prong may be provided, configured for allowing for rotational movement between the respective tooth model and the bracket 40, providing another degree of freedom to the articulator.

In the illustrated embodiment, to disengage the tooth model 100 from the mounting bracket 40, the block 130 may be pulled away from the abutment surface 48. In doing so, the prong elements are deformed inwardly, and this may be done manually or by means of a tool, for example pliers. Alternatively, the prong shoulders may be suitably sloped or rounded, and/or the mouth of the apertures 135 may also be suitable sloped or rounded, so that as the block 130 is pulled away the elements are automatically pushed inwardly in the radial direction.

To further facilitate disengagement, a quick release probe 49 is provided inn each arm 20 for this embodiment. The probe 49 comprises a pushing element (not shown) at the end of a shaft 49a that is reciprocally mounted freely to the mounting bracket 40 in a direction substantially parallel to axis 92, and located generally inbetween the prongs 70. A knob 49b is provided at the projecting end of the shaft 49a. The pushing element is normally accommodated in a recess (not shown) in the abutment surface 48, so as to enable the pushing element to be flush therewith when in the inactive condition. When it is desired to disengage the tooth model 100, the probe 49 is actuated by pushing the same towards the bracket 40, and the pushing element forces the block 130 away from the bracket 40. Once the enlarged portions of the probe have been deformed and are accommodated in the apertures 135, the model 100 may be fully removed from the bracket 40 with relative ease.

In alternative variations of this embodiment, arms 20A, 20B may not necessarily be identical one to another—for example upper arm 20A may comprise a base member that extends away from the lower arm, and lower arm 20B may comprise a substantially longer base member than the upper arm 20A, such that the two arms are hingedly connected at a position, relative to the teeth models 100, that corresponds to the relative position of the condyle axis in the patient. In yet other variations of this embodiment, the articulator comprise one said arm 20, and the other arm does not comprise mount 50, but rather the bracket member is fixed to the base member 30 in a different manner, for example integrally formed or non-movably fixed with respect to one another.

The arms 20 may be made from or comprise any suitable materials or combination of materials, for example metals (including, for example, aluminium, stainless steel, brass, titanium, and so on), plastics (including for example flexible plastics and/or hard plastics), wood, composites, ceramics, and so on.

In use, once the teeth models 100A, 100B are mounted to arms 20A, 20B, respectively, the user may clasp each model 100A 100B with a different hand and the two models may be manipulated and independently displaced and/or rotated with respect to the corresponding base member 30 to provide an envelope of relative positions between the upper and lower teeth models that enables the range, or at least a portion of the range, of real relative positions between the real teeth to be simulated, providing the user with guidance and feedback, which may be useful for example when designing or testing prostheses.

Figure 10:
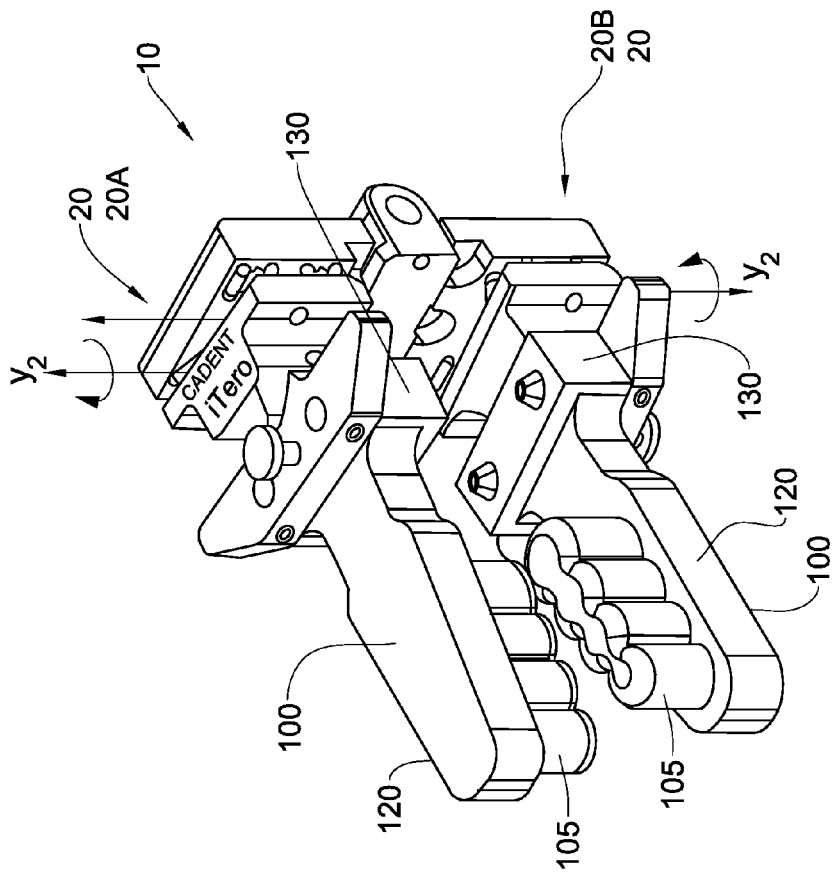
FIG. 10 illustrates in top/front isometric view the embodiment of FIG. 1 in one mode of operation.

Illustrated in FIGS. 10 to 12, are examples of the range of movement provided to the teeth models 100A 100B by mounts 50 in articulator 10. In FIGS. 10 and 11, the teeth models 100A, 100B are rotated in mutually opposed shear directions from side to side and substantially along the occlusal plane, by rotating each teeth model 100 about the respective virtual transverse axis y2, with each respective pair of mount parts 52, 56 in butting and sliding contact at four contact points. The two teeth models 100 may of course be moved by the same or different angular displacements in the same direction by rotating one teeth model about axis y1 and the other about axis y2, or vice versa.

Referring to FIG. 12, the teeth models 100A, 100B are translated in mutually opposed shear directions forwards and backwards, and substantially along the occlusal plane, by rotating the upper teeth model 100A about the respective virtual lateral axis x2, and rotating the lower teeth model 100B about the respective virtual lateral axis x1, with each respective pair of mount parts 52, 56 in butting and sliding contact at four contact points. The two teeth models 100 may of course be mutually displaced in the opposite direction, by rotating the lower teeth model 100B about the respective virtual lateral axis x2, and rotating the upper teeth model 100B about the respective virtual lateral axis x1.

The transverse and/or lateral rotational movements of the teeth models is accomplished against the coupling force provided by the magnetic coupling arrangement 110, and thus, when the manipulations of the teeth models 100 is terminated, the restoring force provided by the magnetic coupling arrangement brings the teeth model and the articulator back to the datum alignment position.

Thus, the transverse and/or lateral rotational movements provided by the mounts 50, together with pivoting movement via axis 99, enables a range of relative movement between an upper and lower teeth model to be provided, which includes simulated movement at or near the occlusal plane.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A dental articulator comprising:
 a first arm hingedly joined to a second arm about a pivot axis, each one of said first arm and said second arm being configured for mounting a dental model thereto, wherein at least one of said first arm and said second arm comprises:
 (a) a bracket member having a distal portion adapted for mounting the respective dental model thereto and a proximal portion, (b) a base member having a distal portion and a proximal portion adapted for hingedly joining said first arm and said second arm, respectively, about said pivot axis, and (c) a magnetic coupling arrangement configured for magnetically affixing the proximal portion of the bracket member to the distal portion of the base member so as to allow the bracket member to rotate with respect to the base member about a rotational axis.

2. An articulator according to claim 1, comprising a model mounting arrangement configured for enabling the respective dental model to be mounted to said respective bracket member, and wherein said model mounting arrangement is different from said magnetic coupling arrangement.

3. An articulator according to claim 1, wherein said magnetic coupling arrangement is comprised in a mount having a first mount part comprised in the base member and a second mount part comprised in the bracket member, and wherein the mount is configured for selectively providing, at least during operation of the articulator, for relative movement between the respective bracket member and the respective base member with respect to a datum alignment position.

4. An articulator according to claim 3, wherein said mount is configured for providing a stable and repeatable relative positioning between the first mount part and the second mount part in said datum alignment position, while permitting relative movement therebetween in at least two degrees of freedom.

5. An articulator according to claim 4, wherein said at least two degrees of freedom include two rotational degrees of freedom.

6. An articulator according to claim 3, wherein said first mount part and second mount part are configured for defining a discrete plurality of contact points therebetween in said datum alignment position, and wherein selective portions of said contact points are disengaged from mutual contact for providing said relative movement.

7. An articulator according to claim 6, comprising a first set of at least four said contact points at said datum alignment position, and a second set of at least four said contact points when carrying out a respective said relative movement.

8. An articulator according to claim 7, wherein at least some of said contact points in said first set are also included in said second set.

9. An articulator according to claim 7, wherein said contact points of said first set are configured for preventing translational movement in at least two degrees of freedom between the first mount part and the second mount part in said datum alignment position.

10. An articulator according to claim 6, wherein each said contact point is provided between a generally hemispherical projection in one of said first and second mount parts, and a generally cylindrical projection in the other one of said first and second mount parts.

11. An articulator according to claim 1, wherein said first arm comprises said bracket member affixed to said first base member via said magnetic coupling arrangement wherein said second arm comprises a bracket member that is adapted for mounting a respective dental model thereto and is different from said bracket member affixed to said first base member, and wherein said bracket member of said second arm is affixed to said second base member via a magnetic coupling arrangement different from said magnetic coupling arrangement with said first base member.

12. An articulator according to claim 1, wherein said magnetic coupling arrangement is configured for elastically affixing the bracket member to the base member.

13. A dental articulator comprising:

a first arm hingedly joined to a second arm about a pivot axis, each said arm adapted for mounting a dental model thereto, wherein at least one of said first arm or second arm comprises:

(a) a bracket member having a proximal portion and a distal portion adapted for mounting the respective dental model thereto, (b) a base member of the arm and having a distal portion for coupling to the bracket member and a proximal portion adapted for hingedly joining said first arm and said second arm, respectively, about said pivot axis, and (c) a mount having a first mount part coupled to the distal portion of the respective base member and a second mount part coupled to the proximal portion of the respective bracket member, wherein the mount is configured for selectively providing, at least during operation of the articulator, for relative movement between the respective bracket member and the respective base member with respect to a datum alignment position, and the mount further comprising a magnetic coupling arrangement configured for coupling the respective bracket member to the respective base member to allow for said relative movement in response to a suitable external force or couple while urging said first mount part into abutting contact with said second mount part to assume said datum alignment position in the absence of the external force or couple.

14. An articulator according to claim 13, wherein said magnetic coupling arrangement is configured for magnetically attracting the bracket member to the base member.

15. An articulator according to claim 14, comprising a model mounting arrangement configured for enabling the dental model to be mounted to said bracket member, and wherein said model mounting arrangement is different from said magnetic coupling arrangement.

16. An articulator according to claim 13, wherein said mount is configured for providing a stable and repeatable relative positioning between the first mount part and the second mount part in said datum alignment position, while permitting relative movement therebetween in at least two degrees of freedom.

17. An articulator according to claim 16, wherein said at least two degrees of freedom include two rotational degrees of freedom.

18. An articulator according to claim 13, wherein said first mount part and second mount part are configured for defining a discrete plurality of contact points therebetween in said datum alignment position, and wherein selective portions of said contact points are disengaged from mutual contact for providing said relative movement.

19. An articulator according to claim 18, wherein each said contact point is provided between a generally hemispherical projection in one of said first and second mount parts, and a generally cylindrical projection in the other one of said first and second mount parts.

20. An articulator according to claim 13, wherein said bracket member comprises a mounting arrangement adapted for reversibly mounting a dental model thereto.

21. An articulator according to claim 20, wherein said mounting arrangement comprises at least one projecting element cantilevered from said bracket member and adapted for reversible engagement with respect to a corresponding aperture provided in said dental model, wherein said at least one projecting element and said corresponding aperture are suitably located such as to provide a desired relative position between said dental model and said pivot axis, at least in said datum position.

22. An articulator according to claim 21, said projecting element comprising a radially deformable free end, said free end having a datum dimension larger than a corresponding internal dimension of said aperture, and being radially deformable from said datum dimension to be at least temporarily accommodated in said aperture when said model is mounted to said bracket member.

23. An articulator according to claim 22, wherein said at least one projecting element is configured such that when said model is mounted thereto, said free end passes through said corresponding aperture and at least partially restores said datum dimension.

24. An articulator according to claim 22, wherein said at least one projecting element comprises a plurality of longitudinal resilient elements circumferentially arranged with respect to a base connected to said bracket member.

25. An articulator according to claim 13, wherein at least one of said first arm or second arm comprises a mechanical stop arrangement to limit pivotal movement of said first arm and said second arm toward one another about said pivot axis.

26. An articulator according to claim 13, wherein said first arm and said second arm are substantially identical with respect to another.

27. A dental articulator comprising:
a first arm hingedly joined to a second arm about a pivot axis, each said arm comprising a bracket member having a proximal portion and a distal portion adapted for mounting the respective dental model thereto,
a first base member of the first arm and a second base member of the second arm, each base member having a distal portion coupling to a proximal portion of a respective bracket member and a proximal portion adapted for hingedly joining said first arm and said second arm, respectively, about said pivot axis, and
a mount configured for kinematically coupling a proximal portion of the bracket member to the distal portion of the first base member or second base member and so as to allow the kinematically coupled respective bracket member to rotate with respect to the respective base member about a rotational axis.

28. A dental articulator, comprising:
a pair of first and second arms substantially identical or symmetrical in structure, each arm comprising:
a bracket member defining a longitudinal arm axis and having a proximal portion and a distal dental portion structured for mounting a dental model;
a base member defining a vertical arm axis and comprising a distal bracket member coupling portion and a proximal hinge end; and
a bracket/base mount assembly comprising a bracket mount part coupled to the bracket member proximal portion, a base mount part coupled to the base member distal portion, and one or more magnetic elements magnetically affixing the proximal portion of the bracket member to the distal portion of the base member so as to allow the bracket member to rotate with respect to the base member about a rotational axis; and
a hinge joining first arm to the second arm about the hinge ends of the respective base members so as to couple the first and second arms about a pivot axis.

* * * * *